US011072832B2

(12) United States Patent
Amini et al.

(10) Patent No.: US 11,072,832 B2
(45) Date of Patent: Jul. 27, 2021

(54) CUSTOMIZED SKIN CARE PRODUCTS AND PERSONAL CARE PRODUCTS BASED ON THE ANALYSIS OF SKIN FLORA (71) Applicant: ProdermIQ, Inc., San Diego, CA (US)

(72) Inventors: Sasan Amini, Redwood City, CA (US); Dana Hosseini, San Diego, CA (US); Eveie W. Schwartz, San Diego, CA (US)

(73) Assignee: PRODERMIQ, INC., San Diego, CA (US)

( * ) Notice: Subject to any disclaimer, the term of this patent is extended or adjusted under 35 U.S.C. 154(b) by 0 days.

(21) Appl. No.: 14/899,048

(22) PCT Filed: Jun. 18, 2014

(86) PCT No.: PCT/US2014/042961
§ 371 (c)(1),
(2) Date: Dec. 16, 2015

(87) PCT Pub. No.: WO2014/205088
PCT Pub. Date: Dec. 24, 2014

(65) Prior Publication Data
US 2016/0122806 A1 May 5, 2016

Related U.S. Application Data (60) Provisional application No. 61/947,316, filed on Mar. 3, 2014, provisional application No. 61/836,589, filed on Jun. 18, 2013.

(51) Int. Cl.
C12Q 1/68 (2018.01)
C12Q 1/689 (2018.01)
G01N 33/569 (2006.01)

(52) U.S. Cl.
CPC ....... C12Q 1/689 (2013.01); G01N 33/56911 (2013.01); C12Q 2600/106 (2013.01); C12Q 2600/112 (2013.01); G01N 2570/00 (2013.01); G01N 2800/20 (2013.01)

(58) Field of Classification Search
CPC .............. C12Q 1/689; C12Q 2600/106; C12Q 2600/112
See application file for complete search history.

(56) References Cited

U.S. PATENT DOCUMENTS

| 6,203,987 | B1 | 3/2001 | Friend et al. |
| 7,827,042 | B2 | 11/2010 | Jung et al. |
| 7,919,250 | B2 | 4/2011 | Blaser et al. |
| 7,927,787 | B2 | 4/2011 | Jung et al. |
| 7,974,856 | B2 | 7/2011 | Jung et al. |
| 7,989,165 | B2 | 8/2011 | Benson |
| 8,000,981 | B2 | 8/2011 | Jung et al. |
| 8,297,028 | B2 | 10/2012 | Jung et al. |
| 8,340,944 | B2 | 12/2012 | Jung et al. |
| 8,468,029 | B2 | 6/2013 | Jung et al. |
| 8,532,938 | B2 | 9/2013 | Jung et al. |
| 8,793,141 | B2 | 7/2014 | Jung et al. |
| 10,169,541 | B2 | 1/2019 | Apte et al. |
| 10,354,756 | B2 | 7/2019 | Apte et al. |
| 10,364,473 | B2 | 7/2019 | Li et al. |
| 10,366,793 | B2 | 7/2019 | Apte et al. |
| 10,381,112 | B2 | 8/2019 | Apte et al. |
| 10,381,117 | B2 | 8/2019 | Apte et al. |
| 10,395,777 | B2 | 8/2019 | Apte et al. |
| 10,410,749 | B2 | 9/2019 | Apte et al. |
| 2007/0202540 | A1 | 8/2007 | Benson |
| 2009/0035329 | A1* | 2/2009 | Blaser ................. A61K 35/74 424/234.1 |
| 2012/0149584 | A1 | 6/2012 | Olle et al. |
| 2013/0121968 | A1 | 5/2013 | Quay |
| 2015/0259728 | A1 | 9/2015 | Cutliffe et al. |
| 2016/0215326 | A1 | 7/2016 | Martin et al. |
| 2017/0235902 | A1 | 8/2017 | Almonacid et al. |
| 2017/0344719 | A1 | 11/2017 | Apte et al. |
| 2018/0030516 | A1 | 2/2018 | Nawana et al. |
| 2018/0137243 | A1 | 5/2018 | Belnap |

(Continued)

FOREIGN PATENT DOCUMENTS

WO WO-2016172196 A1 10/2016
WO WO-2016174677 A1 11/2016

(Continued)

OTHER PUBLICATIONS

Petrosino et al. in Clinical Chemistry 55:5, 856-866 (2009).*
Davey et al. in Nature Reviews/Genetics 12, 499-510 (2011).*
Zhang et al. in Analyst, 137, 293-300 (2012) (Year: 2012).*
Beebe, K. "Is Metabolomics the Rosetta Stone for Understanding the Microbiome?" (https://www.metabolon.com/who-we-are/blog/metabolomics-rosetta-stone-understanding-microbiome) (2017) (Year: 2017).*
The Human Microbiome Project (https://www.bcm.edu/departments/molecular-virology-and-microbiology/research/the-human-microbiome-project (Year: 2012).*

(Continued)

Primary Examiner — Dennis Heyer
(74) Attorney, Agent, or Firm — Wilson Sonsini Goodrich & Rosati (57) ABSTRACT Present invention relate to a combination of experimental and computational workflows that allow characterization of skin and subcutaneous tissue microbial flora and its associated metabolome, aiming to first evaluate an individual's skin and subcutaneous tissue to determine if any skin condition is as a result of an imbalance or absence of commensal or mutualistic microorganisms or their associated metabolites. The methods and the associated computational platform provided herein relate to conducting a customized or personalized test and obtaining customized or personalized information regarding the skin and subcutaneous tissue flora and its associated metabolome there from also have been disclosed.

26 Claims, 3 Drawing Sheets

(56) References Cited

U.S. PATENT DOCUMENTS

| | | |
|---|---|---|
| 2019/0050534 A1 | 2/2019 | Apte et al. |
| 2019/0213226 A1 | 7/2019 | Ludwinski et al. |
| 2019/0237194 A1 | 8/2019 | Salvi et al. |
| 2019/0292577 A1 | 9/2019 | Amini et al. |

FOREIGN PATENT DOCUMENTS

| | | |
|---|---|---|
| WO | WO-2017049103 A1 | 3/2017 |
| WO | WO-2017109059 A1 | 6/2017 |
| WO | WO-2017189614 A1 | 11/2017 |
| WO | WO-2019191141 A1 | 10/2019 |

OTHER PUBLICATIONS

Paliwal et al., "Diagnostic Opportunities Based on SkinBiomarkers," Eur. J. Pharm. Sci. (2013), 50:546-556, Elsevier.

Extended European Serarch Report dated Feb. 1, 2017 regarding EP 14813865.4.

Fitz-Gibbon, Sorel et al.: "Propionibacterium acnes Strain Populations in the Human Skin Microbiome Associated with Acne"; Journal of Investigative Dermatology, vol. 133, No. 9, Jan. 2013, pp. 2152-2160.

Grice, E. A. et al.: "Topographical and Temporal Diversity of the Human Skin Microbiome"; Science, vol. 324, No. 5931, May 2009, pp. 1190-1192.

Kong, Heidi H.: "Skin microbiome: genomics-based insights into the diversity and role of skin microbes"; Molecular medicine today, vol. 17, No. 6, Jun. 2011, pp. 320-328.

Morgan, Xochitl C. et al.: "Chapter 12: Human Microbiome Analysis"; PLoS Computational Biology, vol. 8, No. 12, Dec. 2012, p. e1002808, 14 pages.

Peterson, J. et al.: "The NIH Human Microbiome Project"; Genome Research, vol. 19, No. 12, Oct. 2009, pp. 2317-2323.

Baehrecke, EH. Autophagic programmed cell death in Drosophila. Cell Death Differ. 10(9):940-945 (2003).

Bartel, DP. MicroRNAs: genomics, biogenesis, mechanism, and function. Cell. 116(2): 281-297 (2003).

Brennecke et al., "Bantam encodes a developmentally regulated microRNA that controls cell proliferation and regulates the proapoptotic gene hid in Drosophila," Cell, 113: 25-36 (2003).

Brown et al., The Formulation of Bacteriophage in a Semi Solid Preparation for Control of Propionibacteriumacnes Growth. PLoS One. 11(3):e0151184 (2016).

Chen et al. MicroRNAs modulate hematopoietic lineage differentiation. Science 303(5654):83-86 (2004).

Lee et al. The C. elegans heterochronic gene lin-4 encodes small RNAs with antisense complementarity to lin-14. Cell 75:843-854 (1993).

Mills et al., Comparing 2.5%, 5%, and 10% benzoyl peroxide on inflammatory acne vulgaris. International Journal of Dermatology. 25(10):664-667 (1986).

PCT/US2019/024144 International Search Report an Written Opinion dated Jun. 24, 2019.

Pending U.S. Appl. No. 16/492,079 filed Sep. 6, 2019.

Reinhart et al. The 21-nucleotide let-7 RNA regulates developmental timing in Caenorhabditis elegans. Nature 403(6772):901-906 (2000).

Yi et al. Morphogenesis in skin is governed by discrete sets of differentially expressed microRNAs. Nature Genetics 38(3):356-362 (2006).

Australian Patent Application No. 2014281553 Office Action dated Feb. 12, 2020.

Baylor College of Medicine. The Human Microbiome Project. Available at: https://www.bcm.edu/departments/molecular-virology-and-microbiology/research/the-human-microbiome-project (2012).

Grice et al. The skin mirobiome. Nat Rev Microbiol 9(4):244-253 (2011).

Pray et al., Study of Human Mirobiome. The Human Microbiome, Diet, and Health: Workshop. The National Academies Press (US), Washington, DC. vol. 2, ISBN 978-0-309-26585-0: pp. 33-54 (2013).

Turnbaugh et al., The Human Microbiome Project. Nature 449: 804-810 (2007).

Peterson, The NIH Human Microbiome Project. Genome Research 19: 2317-2323 (2009).

Clear Skin Probiotic Cleaner 250mL, Eminence Organic Skin Care. (2013).

European Application No. 19219640 Search Report dated Sep. 1, 2020.

Kong et al. Temporal shifts in the skin microbiome associated with disease flares and treatment in children with atopic dermatitis. Genome Res 22(5):850-859 (2012).

Larsen et al., Metabolome of human gut microbiome is predictive of host dysbiosis. Gigascience 4(1) 16 pages (2015).

PCT/US2019/024144 International Preliminary Report on Patentability dated Sep. 29, 2020.

Shaffer et al., Microbiome and metabolome data integration provides insight into health and disease. Transl Res 189: 51-64 (2017).

Yang et al., Integrating '-omics' and natural product discovery platforms to investigate metabolic exchange in microbiomes. Current Opinion in Chemical Biology 15(1): 79-87 (2011).

* cited by examiner

CUSTOMIZED SKIN CARE PRODUCTS AND PERSONAL CARE PRODUCTS BASED ON THE ANALYSIS OF SKIN FLORA

CROSS REFERENCE TO RELATED APPLICATION(S)

This application is a 35 USC § 371 National Stage application of International Application No. PCT/US2014/042961, filed Jun. 18, 2014, which claims the benefit of U.S. Application Ser. No. 61/947,316, filed Mar. 3, 2014, and U.S. Application Ser. No. 61/836,589, filed Jun. 18, 2013, each of which is incorporated by reference herein in its entirety.

BACKGROUND OF THE INVENTION

Field of the Invention

The present invention is based generally on skin care products and more specifically on methods of analyzing skin and subcutaneous tissue flora and its associated metabolome to develop or identify personalized skin care products.

Background Information

About 100 trillion microorganisms live in and on the human body vastly outnumbering the body's approximately 10 trillion human cells. These normally harmless viruses, bacteria and fungi are referred to as commensal or mutualistic organisms. Commensal and mutualistic organisms help keep our bodies healthy in many ways: they help us to digest foods and acquire nutrients such as vitamins B and K, encourage the immune system to develop and prevent the colonization of, for example, bacterial pathogens that cause disease by competing with them. Together all of the microorganisms living in and on the body—commensal, mutualistic and pathogenic—are referred to as the microbiome and their equilibrium and associated metabolome is closely linked to an individual's health status and vice-versa.

Next generation sequencing (NGS) has created an opportunity to quickly and accurately identify and profile the microbiome inhabiting the skin and subcutaneous tissue, which then creates an opportunity for the creation of customized or personalized skin care and personal care products that either maintains a healthy microbiome or shifts a profile towards a healthy equilibrium or profile by blending a mixture of commensal and/or mutualistic organisms specifically created to establish a healthy profile. The optimal flora also interacts with the host immune system in a synergistic way further propagating its health benefits. The associated metabolome of individuals can also be profiled either by a mass-spectrometry based system or using genomics-based metabolome modeling and flux-balance analysis and used to make a healthy metabolome profile. Deficiencies in any of the beneficial metabolites can be supplemented as well.

Currently, the only way to treat dermatological conditions is through antibiotics that drastically impact the microbiome including the commensal and mutualistic bacteria or through anti-inflammatory agents that attenuate body's immune response and alleviate the epidermal cell's response to pathogens, but may fail to address the underlying cause of a skin condition if it is due to an imbalance or absence of commensal or mutualistic microorganisms, overabundance of opportunistic or pathogenic bacteria, or deficiencies of essential or beneficial metabolites.

SUMMARY OF THE INVENTION

The invention relates generally to the development of customized skin care and personal care products for human and animal use and, more particularly, but not by way of limitation, to the development of personal care products that are based on the initial evaluation of the flora inhabiting the skin and subcutaneous tissue. The present disclosure relates to the methods for analyzing the skin and subcutaneous tissue flora, e.g., the microbiome, and its associated metabolome, comparing the resulting profile of the skin and subcutaneous tissue flora and metabolome to a healthy profile, represented as a quantity and diversity of flora that falls within a range determined from a set of healthy skin types, and then customizing skin care and personal care products that will augment the flora residing on a test subject's skin and subcutaneous tissue and its associated metabolome or replicate a healthy flora profile on to that of a test subject.

Accordingly, in one aspect, the invention provides a method of characterizing a microbiome of skin or subcutaneous tissue of a subject. The method includes: a) obtaining a sample comprising a plurality of microorganisms from the skin or subcutaneous tissue of the subject; and b) analyzing and classifying the plurality of microorganisms of (a) to characterize the microbiome of the subject, thereby characterizing the microbiome of the subject. In some embodiments, the method further includes comparing the microbiome of the subject to a reference microbiome or generating a microbiome profile of the subject, or identifying a disease or disorder which the subject has, or is at risk of developing, or providing a personalized treatment regime to the subject. In various embodiments, the reference microbiome is classified as having a healthy profile and a similarity between the microbiome of the subject and the reference microbiome identifies the microbiome of the subject as having a healthy profile. Alternatively, the reference microbiome is classified as having, or at risk of having a disease or disorder and a similarity between the microbiome of the subject and the reference microbiome identifies the microbiome of the subject as having as having, or at risk of having the disease or disorder.

In another aspect, the invention provides a method of characterizing microbiomes of skin or subcutaneous tissue of a plurality of subjects. The method includes: a) obtaining a plurality of samples from the skin or subcutaneous tissue of the plurality of subjects, each sample comprising a plurality of microorganisms; and b) analyzing and classifying the plurality of microorganisms of each sample of (a) to identify a microbiome of each of the plurality of samples, thereby characterizing the microbiomes of the plurality of subjects. In embodiments, the method further includes clustering the results of (b) to identify individual cohorts of the plurality of samples. In some embodiments, the each individual cohort exhibits a particular phenotype or profile. In some embodiments, each individual cohort includes samples having similar microbiomes, samples from subjects having a common skin disease or disorder, or samples from subjects having a similar metabolite profile.

In yet another aspect, the present invention provides a method of diagnosing a disease or disorder in a subject. The method includes a) obtaining a sample comprising a plurality of microorganisms from the skin or subcutaneous tissue of the subject; b) analyzing and classifying the plurality of microorganisms of (a) to identify a microbiome of the subject; and c) comparing the microbiome of the subject to a reference microbiome representative of a microbiome of a subject having or at risk of the disease or disorder, wherein a similarity between the microbiome of the subject and the reference microbiome is indicative of the subject being at risk of, or having the disease or disorder, thereby diagnosing a disease or disorder in the subject. In embodiments the method further includes providing a personalized treatment regime to the subject. In some embodiments the method further includes formulating and administering a customized therapeutic formulation to the subject.

In another aspect, the invention provides a method of formulating a customized therapeutic formulation for a subject having, or at risk of a disease or disorder. The method includes: a) obtaining a sample comprising a plurality of microorganisms from the skin or subcutaneous tissue of the subject; b) analyzing and classifying the plurality of microorganisms of (a) to identify a microbiome of the subject; c) comparing the microbiome of the subject to a reference microbiome representative of a microbiome of a subject having or at risk of the disease or disorder, wherein a similarity between the microbiome of the subject and the reference microbiome is indicative of the subject being at risk of, or having the disease or disorder; and d) formulating a customized therapeutic formulation based on (c), thereby formulating a customized therapeutic formulation.

In another aspect, the invention provides a therapeutic formulation formulated via the method of the invention.

BRIEF DESCRIPTION OF THE DRAWINGS

FIG. 1 is a high-level summary of experimental and analysis pipeline for profiling skin and subcutaneous tissue flora. Informative regions of the microbial genome from a mixed population collected from a skin or subcutaneous tissue sample are amplified with universal primer sequences designed to capture maximum diversity of various bacterial species. The amplified regions are uniquely indexed to allow multiplex processing of samples from various sources (Nucleic Acid Harvesting and Prep). Amplified regions from different sources can be combined and sequenced with the Paired End (PE) mode on a NGS platform or alternatively can be analyzed on Sanger-sequencing, mass-spectrometry, quantitative PCR, immunofluorescence, in situ hybridization, or microbial staining based platform. Raw output of the identification platform is analyzed using a proprietary analysis pipeline that assigns the raw read-outs to species from different taxonomy groups. A similar workflow would be utilized for mapping metabolites associated with any given sample.

DETAILED DESCRIPTION OF THE INVENTION

Figure 1:
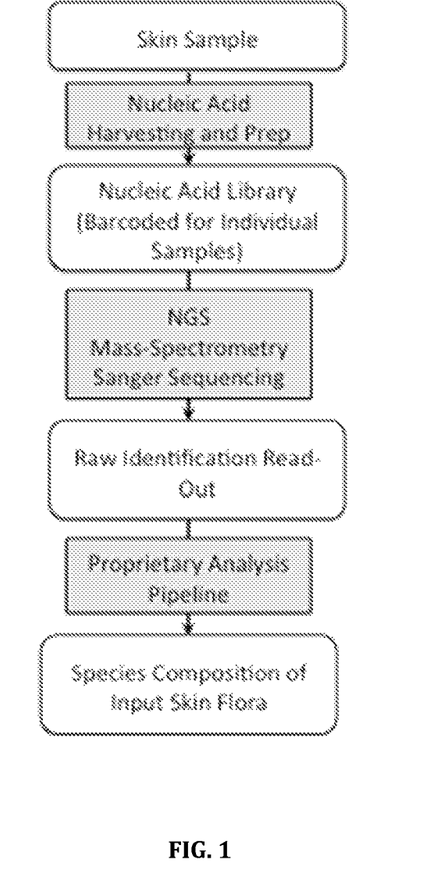
Figure 2:
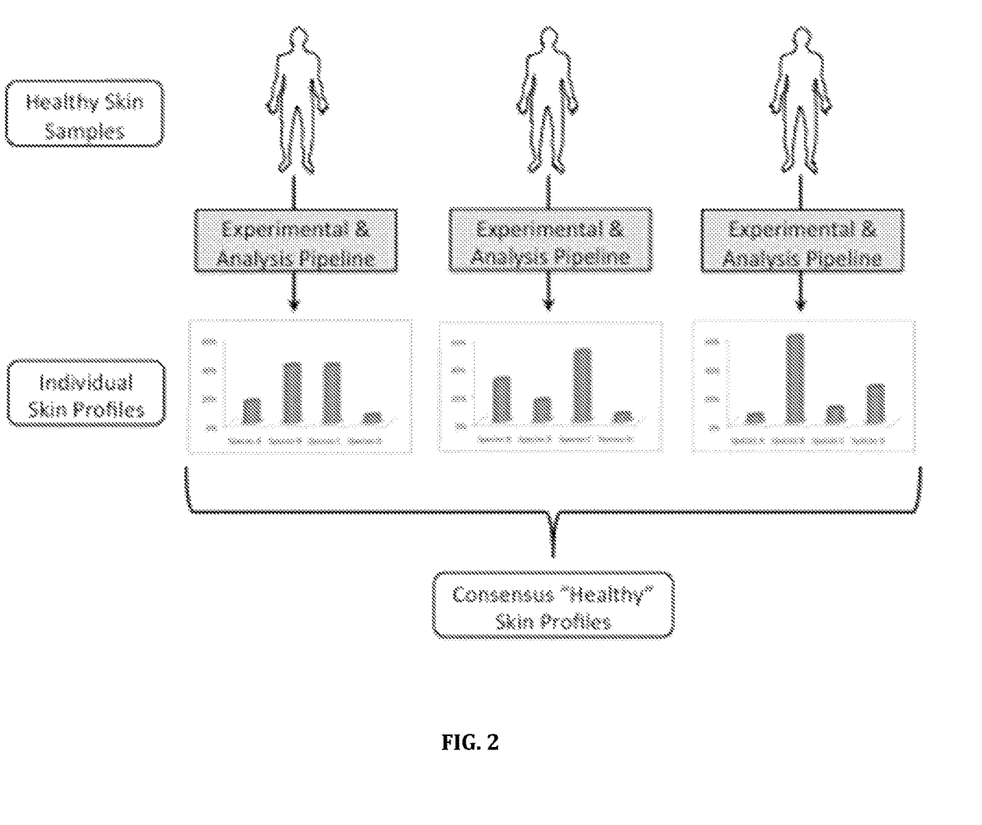
FIG. 2 shows multiple samples from a healthy cohort of individuals are collected and samples are processed as described in FIG. 1 through our pipeline and used to build a consensus profile for the healthy population, capturing the constituent dominant species flora or their associated metabolome. The healthy profile is treated as the reference to compare any affected group, population or individual.
Figure 3:
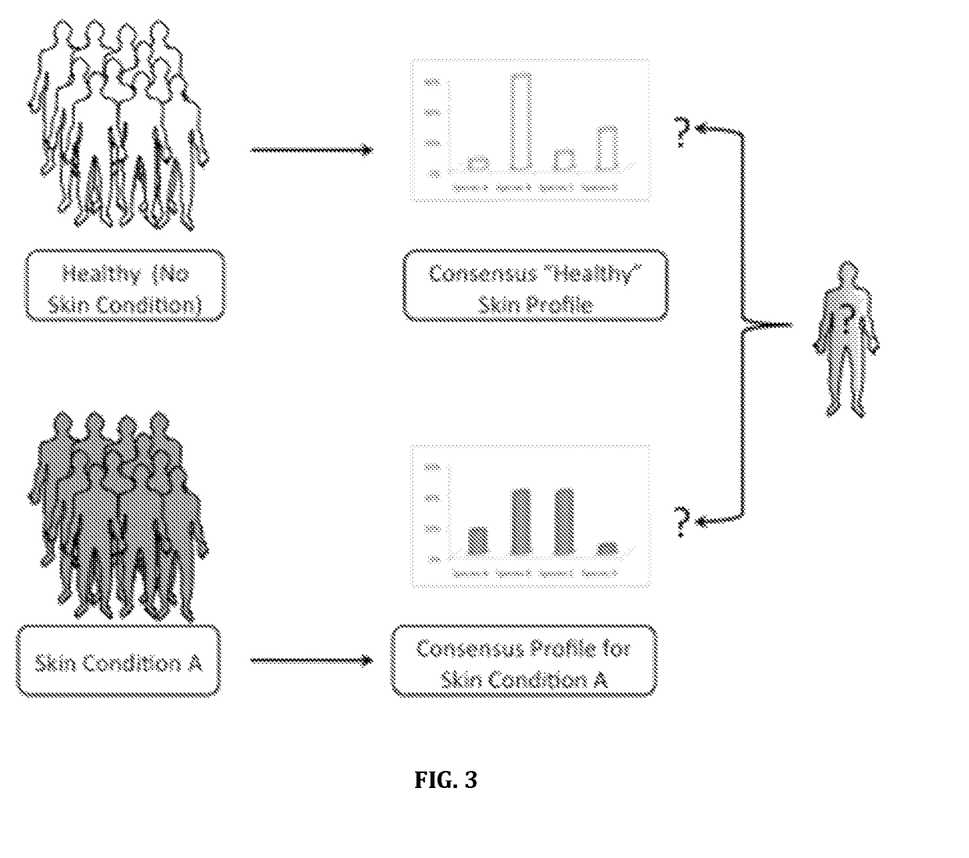
FIG. 3 shows multiple samples from a cohort of individuals with one characteristic skin condition will be collected and their skin flora and its associated metabolome is profiled as described previously. The species meta-data profile is used to identify signature microorganisms or metabolites which are causative of or associated with that skin condition. Contrasted with the healthy profile identified before, any anomaly in skin and subcutaneous tissue flora or metabolome composition of a new client (shown by a question mark in the figure) can be detected even at early stages and can be fixed or remediated with a customized or personalized skin care product which shifts that affected profile towards a healthy equilibrium created by blending a mixture of commensal organism or metabolites specifically expected to establish a healthy profile.

It is now well established that about 100 trillion microorganisms live in and on the human body vastly outnumbering the approximately 10 trillion human cells. These normally harmless viruses, bacteria and fungi are referred to either as commensals (are not harmful to their host) or mutualistic (offer a benefit). Commensal and mutualistic organisms help keep our bodies healthy in many ways: they help us to digest foods and acquire nutrients such as vitamins B and K, encourage our immune system to develop and prevent the colonization of, for example, bacterial pathogens that cause disease by competing with them. Together all of the microorganisms—commensal, mutualistic and pathogenic—are referred to as the body's microbiome and their equilibrium and associated microbiome is closely linked to an individual's health status and vice-versa.

Currently, the primary means of treating dermatological conditions is through antibiotics that drastically alter an individual's microbiome or through anti-inflammatory agents that attenuate body's immune response alleviating the epidermal cell's response to pathogens, but failing to address the underlying cause of a skin condition. Embodiments of the present invention relate to a combination of experimental and computational workflows that allow characterization of skin microbial flora and its associated metabolome, aiming to first evaluate an individual's skin to determine if their skin condition is a result of an imbalance or absence of commensal or mutualistic microorganisms or its associated metabolome.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The invention relates generally to the development of customized skin care and personal care products for human and animal use and, more particularly, but not by way of limitation, to the development of personal care products that are based on the initial evaluation of the flora inhabiting the skin and subcutaneous tissue. The present disclosure relates to the methods for analyzing the skin and subcutaneous tissue flora and its associated metabolome, comparing the resulting profile of the skin and subcutaneous tissue flora and metabolome to a healthy profile, represented as a quantity and diversity of flora that falls within a range determined from a set of healthy skin types, and then customizing skin care and personal care products that will augment the flora residing on a test subject's skin and subcutaneous tissue and its associated metabolome or replicate a healthy flora profile on to that of a test subject.

The individualized skin test result may be the basis for development of individualized skin care and personal care products which are customized to either maintain a healthy skin microbiome and metabolome or shift a profile towards a healthy equilibrium or profile by adding one or more commensal and/or mutualistic organisms and/or substrates that favor the growth of commensal and mutualistic organisms on the skin. The exact composition of the skin care product blend may be determined after comparing the resulting profile of any individual's skin and subcutaneous tissue flora and metabolome to a healthy profile and then customizing skin care and personal care products that best shift the subject's skin and subcutaneous tissue flora and metabolome toward a healthy profile. The optimal flora and substrates and metabolomes would also synergize with host's immune system and contribute toward a healthy skin from that perspective.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Accordingly, in one aspect, the invention provides a method of characterizing a microbiome of skin or subcutaneous tissue of a subject. The method includes: a) obtaining a sample comprising a plurality of microorganisms from the skin or subcutaneous tissue of the subject; and b) analyzing and classifying the plurality of microorganisms of (a) to characterize the microbiome of the subject, thereby characterizing the microbiome of the subject.

As used herein, the terms "sample" and "biological sample" refer to any sample suitable for the methods provided by the present invention. A sample of cells can be any sample, including, for example, a skin or subcutaneous tissue sample obtained by non-invasive techniques such as tape stripping, scraping, swabbing, or more invasive techniques such as biopsy of a subject. In one embodiment, the term "sample" refers to any preparation derived from skin or subcutaneous tissue of a subject. For example, a sample of cells obtained using the non-invasive method described herein can be used to isolate nucleic acid molecules or proteins for the methods of the present invention. Samples for the present invention may be taken from an area of the skin shown to exhibit a disease or disorder, which is suspected of being the result of a disease or a pathological or physiological state, such as psoriasis or dermatitis, or the surrounding margin or tissue. As used herein, "surrounding margin" or "surrounding tissue" refers to tissue of the subject that is adjacent to the skin shown to exhibit a disease or disorder, but otherwise appears to be normal.

In some embodiments, the method further includes comparing the microbiome of the subject to a reference microbiome or generating a microbiome profile of the subject, or identifying a disease or disorder which the subject has, or is at risk of developing, or providing a personalized treatment regime to the subject. In various embodiments, the reference microbiome is classified as having a healthy profile and a similarity between the microbiome of the subject and the reference microbiome identifies the microbiome of the subject as having a healthy profile. Alternatively, the reference microbiome is classified as having, or at risk of having a disease or disorder and a similarity between the microbiome of the subject and the reference microbiome identifies the microbiome of the subject as having as having, or at risk of having the disease or disorder.

As used herein "a healthy profile" refers to a microbiome associated with a sample from a subject that is from a subject that is determined to have a healthy microbiome, e.g., free from disease or disorder, or risk thereof. As such, in one embodiment, the reference microbiome is that of a sample of cells obtained from a healthy individual that does not have a skin disorder or particular undesirable phenotype.

The term healthy profile refers a quantity and diversity of flora that falls within a range determined from a set of healthy skin types. The term healthy skin refers to skin that is devoid of a skin condition, disease or disorder, including, but not limited to inflammation, rash, dermatitis, atopic dermatitis, eczema, psoriasis, dandruff, acne, cellulitis, rosacea, warts, seborrheic keratosis, actinic keratosis, tinea versicolor, viral exantham, shingles, ringworm, and cancer, such as basal cell carcinoma, squamous cell carcinoma, and melanoma.

Additionally, as used herein, a "disease" or "disorder" is intended to generally refer to any skin associated disease, for example, but in no way limited to, inflammation, rash, dermatitis, atopic dermatitis, eczema, psoriasis, dandruff, acne, cellulitis, rosacea, warts, seborrheic keratosis, actinic keratosis, tinea versicolor, viral exantham, shingles, ringworm, and cancer, such as basal cell carcinoma, squamous cell carcinoma, and melanoma.

The term "cancer" as used herein, includes any malignant tumor including, but not limited to, carcinoma, melanoma and sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof. The term "cancerous cell" as provided herein, includes a cell afflicted by any one of the cancerous conditions provided herein. The term "carcinoma" refers to a malignant new growth made up of epithelial cells tending to infiltrate surrounding tissues, and to give rise to metastases. The term "melanoma" refers to a malignant tumor of melanocytes which are found predominantly in skin but also in bowel and the eye. "Melanocytes" refer to cells located in the bottom layer, the basal lamina, of the skin's epidermis and in the middle layer of the eye. Thus, "melanoma metastasis" refers to the spread of melanoma cells to regional lymph nodes and/or distant organs (e.g., liver, brain, breast, prostate, etc.).

The term "skin" or "subcutaneous tissue" refers to the outer protective covering of the body, consisting of the epidermis (including the stratum corneum) and the underlying dermis, and is understood to include sweat and sebaceous glands, as well as hair follicle structures and nails. Throughout the present application, the adjective "cutaneous" and "subcutaneous" can be used, and should be understood to refer generally to attributes of the skin, as appropriate to the context in which they are used. The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

As discussed further herein, Next Generation Sequencing, or NGS, a powerful DNA sequencing technology that allows for the rapid and accurate sequencing of cells or organisms, now enables evaluating complex bacterial communities, a good example of which is the microbiome. The present invention envisions identification of inhabitant flora for every individual to be conducted on such a Next Generation Sequencing (NGS) platform. Such platform allow one to quickly and accurately identify and profile the microbiome inhabiting the skin with high enough sensitivity and specificity with a relatively short turn-around time and scalable throughput. Alternatively, a Sanger-sequencing, mass-spectrometry, quantitative PCR, immunofluorescence, in situ hybridization, or microbial staining based platform can be used to characterize individual profiles. Similarly, the microbiome or metabolome can be profiled either by a mass-spectrometry based system or using genomics-based metabolome modeling and flux-balance analysis. All the above-mentioned identification methods can be implemented on samples directly collected from individuals without any proliferation step. This way, minimal bias is introduced toward identification of a mixture of culturable and unculturable microorganisms or their associated metabolome.

By leveraging the high throughput capabilities of NGS or other microbial identification methods like mass spectrometry or Sanger sequencing, hundreds of microorganisms on an individual's subcutaneous tissue and their associated microbiome and metabolome will simultaneously be identified and the resulting profile may be compared to a healthy profile from a database of skin and subcutaneous tissue profiles. Independent of which platform is exploited for profiling, the abovementioned platform may be offered as a test to any client and the output may be used to identify which commensal, pathogenic, or mutualistic microorganisms or their associated metabolite are depleted or overrepresented on the subject's skin and subcutaneous tissue compared to the healthy profile.

Furthermore, the composition of subject's flora and metabolome may be compared to previously complied database of different skin conditions to see whether he or she is prone to develop any of those skin conditions in future. Based on the customized or personalized test results, a customized or personalized skin care or personal care blend may be formulated for that individual by blending a mixture of commensal and mutualistic microorganisms or their relevant metabolites that are depleted in that individual's flora or metabolome with or without the necessary substrates and nutrients that favor proliferation of commensal and mutualistic organisms. This customized or personalized skin care or personal care product is specifically created in a way to establish an optimal profile by either maintaining a healthy microbiome or shifting the suboptimal profile towards a healthy equilibrium. Also the synergies between the optimal microbial flora and its associated metabolome and host's immune system will further contribute to skin health and wellness.

As such the methods and platforms described herein may utilize analysis of a nucleic acid molecule, such as sequencing a nucleic acid molecule. Sequencing methods may include whole genome sequencing, next generation sequencing, Sanger-sequencing, 16S rDNA sequencing and 16S rRNA sequencing. Further, such methods and platforms described herein may utilize mass-spectrometry, quantitative PCR, immunofluorescence, in situ hybridization, a microbial staining based platform, or combination thereof.

In embodiments, the input to the identification platform can be any nucleic acid, including DNA, RNA, cDNA, miRNA, mtDNA, single or double-stranded. This nucleic acid can be of any length, as short as oligos of about 5 bp to as long a megabase or even longer. As used herein, the term "nucleic acid molecule" means DNA, RNA, single-stranded, double-stranded or triple stranded and any chemical modifications thereof. Virtually any modification of the nucleic acid is contemplated. A "nucleic acid molecule" can be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule. For methods that analyze expression of a gene, the nucleic acid isolated from a sample is typically RNA.

Micro-RNAs (miRNA) are small single stranded RNA molecules an average of 22 nucleotides long that are involved in regulating mRNA expression in diverse species including humans (reviewed in Bartel 2004). The first report of miRNA was that of the lin-4 gene, discovered in the worm *C. elegans* (Lee, Feinbaum et al. 1993). Since then hundreds of miRNAs have been discovered in flies, plants and mammals. miRNAs regulate gene expression by binding to the 3'-untranslated regions of mRNA and catalyze either i) cleavage of the mRNA; or 2) repression of translation. The regulation of gene expression by miRNAs is central to many biological processes such as cell development, differentiation, communication, and apoptosis (Reinhart, Slack et al. 2000; Baehrecke 2003; Brennecke, Hipfner et al. 2003; Chen, Li et al. 2004). Recently it has been shown that miRNA are active during embryogenesis of the mouse epithelium and play a significant role in skin morphogenesis (Yi, O'Carroll et al. 2006).

Given the role of miRNA in gene expression it is clear that miRNAs will influence, if not completely specify the relative amounts of mRNA in particular cell types and thus determine a particular gene expression profile (i.e., a population of specific mRNAs) in different cell types. In addition, it is likely that the particular distribution of specific miRNAs in a cell will also be distinctive in different cell types. Thus, determination of the miRNA profile of a tissue may be used as a tool for expression profiling of the actual mRNA population in that tissue. Accordingly, miRNA levels and/or detection of miRNA mutations are useful for the purposes of disease detection, diagnosis, prognosis, or treatment-related decisions (i.e., indicate response either before or after a treatment regimen has commenced) or characterization of a particular disease in the subject.

As used herein, the term "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration.

A "probe" or "probe nucleic acid molecule" is a nucleic acid molecule that is at least partially single-stranded, and that is at least partially complementary, or at least partially substantially complementary, to a sequence of interest. A probe can be RNA, DNA, or a combination of both RNA and DNA. It is also within the scope of the present invention to have probe nucleic acid molecules comprising nucleic acids in which the backbone sugar is other that ribose or deoxyribose. Probe nucleic acids can also be peptide nucleic acids. A probe can comprise nucleolytic-activity resistant linkages or detectable labels, and can be operably linked to other moieties, for example a peptide.

A single-stranded nucleic acid molecule is "complementary" to another single-stranded nucleic acid molecule when it can base-pair (hybridize) with all or a portion of the other nucleic acid molecule to form a double helix (double-stranded nucleic acid molecule), based on the ability of guanine (G) to base pair with cytosine (C) and adenine (A) to base pair with thymine (T) or uridine (U). For example, the nucleotide sequence 5'-TATAC-3' is complementary to the nucleotide sequence 5'-GTATA-3'.

As used herein "hybridization" refers to the process by which a nucleic acid strand joins with a complementary strand through base pairing. Hybridization reactions can be sensitive and selective so that a particular sequence of interest can be identified even in samples in which it is present at low concentrations. In an in vitro situation, suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

As used herein, the term "skin flora" or "microbiome" refers to microorganisms, including bacteria, viruses, and fungi that inhabit the skin or subcutaneous tissues of the subject.

As used herein, the terms microbial, microbe, or microorganism refer to any microscopic organism including prokaryotes or eukaryotes, bacterium, archaebacterium, fungus, virus, or protist, unicellular or multicellular.

As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. Thus, a "treatment regimen" refers to any systematic plan or course for treating a disease or cancer in a subject.

In embodiments, nucleic acid molecules can also be isolated by lysing the cells and cellular material collected from the skin sample by any number of means well known to those skilled in the art. For example, a number of commercial products available for isolating polynucleotides, including but not limited to, RNeasy™ (Qiagen, Valencia, Calif.) and TriReagent™ (Molecular Research Center, Inc, Cincinnati, Ohio) can be used. The isolated polynucleotides can then be tested or assayed for particular nucleic acid sequences, including a polynucleotide encoding a cytokine. Methods of recovering a target nucleic acid molecule within a nucleic acid sample are well known in the art, and can include microarray analysis.

As discussed further herein, nucleic acid molecules may be analyzed in any number of ways known in the art that may assist in determining the microbiome and/or metabolome associated with an individual's skin. For example, the presence of nucleic acid molecules can be detected by DNA-DNA or DNA-RNA hybridization or amplification using probes or fragments of the specific nucleic acid molecule. Nucleic acid amplification based assays involve the use of oligonucleotides or oligomers based on the nucleic acid sequences to detect transformants containing the specific DNA or RNA.

In another embodiment, antibodies that specifically bind the expression products of the nucleic acid molecules of the invention may be used to characterize the skin lesion of the subject. The antibodies may be used with or without modification, and may be labeled by joining them, either covalently or non-covalently, with a reporter molecule.

A wide variety of labels and conjugation techniques are known by those skilled in the art and may be used in various nucleic acid and amino acid assays. Means for producing labeled hybridization or PCR probes for detecting sequences related to the nucleic acid molecules of Tables 1-6 include oligolabeling, nick translation, end-labeling or PCR amplification using a labeled nucleotide. Alternatively, the nucleic acid molecules, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated. In situ PCR may be utilized for the direct localization and visualization of target nucleic acid molecules and may be further useful in correlating expression with histopathological finding.

Means for producing specific hybridization probes for nucleic acid molecules of the invention include the cloning of the nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

The term "skin care product" or "personal care product" refers to skin care products and includes, but is not limited to, cleansing products, shampoo, conditioner, toners or creams, topical ointments and gels, as well as localized (e.g. under eye) gel, all of which may be formulated to contain ingredients specifically designed to shift microbial population to a healthy profile with or without a commensal or mutualistic organism or mixture of commensal or mutualistic organisms in either an active or dormant state. Such skin care products may further include therapeutic agents, vitamins, antioxidants, minerals, skin toning agents, polymers, excipients, surfactants, probiotics or fraction thereof, microorganism or product from the culture thereof, such a bacteria, fungi and the like, either living, dormant or inactive.

"Skin commensal microorganisms" means both prokaryotes and eukaryotes that may colonize (i.e., live and multiply on human skin) or temporarily inhabit human skin in vitro, ex vivo and/or in vivo. Exemplary skin commensal microorganisms include, but are not limited to, Alphaproteobacteria, Betaproteobacteria, Gammaproteobacteria, *Propionibacteria, Corynebacteria, Actinobacteria, Clostridiales, Lactobacillales, Staphylococcus, Bacillus, Micrococcus, Streptococcus, Bacteroidales, Flavobacteriales, Enterococcus, Pseudomonas, Malassezia, Maydida, Debaroyomyces,* and *Cryptococcus.*

*P. acnes* is a commensal, non-sporulating bacilliform (rod-shaped), gram-positive bacterium found in a variety of locations on the human body including the skin, mouth, urinary tract and areas of the large intestine. *P. acnes* can consume skin oil and produce byproducts such as short-chain fatty acids and propionic acid, which are known to help maintain a healthy skin barrier. Propionibacteria such as *P. acnes* also produce bacteriocins and bacteriocin-like compounds (e.g., propionicin P1G-1, jenseniin G, propionicins SM1, SM2 T1, and acnecin), which are inhibitory toward undesirable lactic acid-producing bacteria, gram-negative bacteria, yeasts, and molds. In embodiments, a subject having skin identified as having *P. acnes* may be treated with a personal care product designed to inhibit growth and proliferation of *P. acnes.*

In embodiments, an individual's skin profile is translated into a personalized SkinIQ™ index, which is an overall snapshot of skin health, by capturing both the diversity of skin flora and its eminence to assist in formulating a personal care product. The main factor contributing to eminence is probiotic balance, the ratio of mutualistic and commensal microorganisms to (opportunistic) pathogens. However eminence could also comprise other factors that could positively impact the health of skin. These factors could include presence of key biosynthetic microbial genes, gene products or proteins responsible for the promotion or maintenance of healthy host skin. All these factors will contribute to the collective health of skin by, but not limited to, the reduction of skin inflammation, the reduction of the relative amounts of pathogens, and the biosynthesis of pro-vitamins, antimicrobial peptides, vitamins and fatty acids. The combination of diversity and eminence, represented by SkinIQ™ index, can also be a predictive measure of skin health. For example, the a preponderance of a certain subspecies of Propionibacterium acnes may be strongly associate with risk of acne breakout. Similarly, SkinIQ™ may be predictive of flare ups of other skin conditions including, but not limited to, eczema, psoriasis, atopic dermatitis and rosacea.

The SkinIQ™ index is defined under Skin Health Measurement System that contrasts any individual profile to the "consensus healthy profile" from a database of skin profiles (microbiomes and/or metabolomes) and places every profile within the healthy population context. The consensus healthy profile is defined separately for each bacterial species. The data from the healthy population is used to define the range where any given bacterial species is expected to be found within healthy individuals. All these ranges define a reference for future comparisons. The Skin Health Measurement System™ further serves as a powerful discovery tool that can be used to mine a rich data set for novel microbes that can be utilized in skin care formulations to positively impact different skin conditions including, but not limited to acne, atopic dermatitis, psoriasis and eczema. Also it can be used to mine higher-level interactions between different bacterial species, with potential therapeutic implications.

As such, the invention contemplates generating a reference database containing a number of reference projected profiles created from skin samples of subjects with known states, such as normal or healthy skin, as well as various skin disease states. The individuals profile may be compared with the reference database containing the reference profiles. If the profile of the subject matches best with the profile of a particular disease state in the database, the subject is diagnosed as having such disease state. Various computer systems and software can be utilized for implementing the analytical methods of this invention and are apparent to one of skill in the art. Exemplary software programs include, but are not limited to, Cluster & TreeView (Stanford, URLs: rana.lbl.gov or microarray.org), GeneCluster (MIT/Whitehead Institute, URL: MPR/GeneCluster/GeneCluster.html), Array Explorer (SpotFire Inc, URL: spotfire.com/products/scicomp.asp #SAE) and GeneSpring (Silicon Genetics Inc, URL: sigenetics.com/Products/GeneSpring/index.html) (for computer systems and software, see also U.S. Pat. No. 6,203,987, incorporated herein by reference).

In an embodiment, the invention provides a method of characterizing skin and/or subcutaneous tissue comprising collecting a sample from a subject containing skin or subcutaneous tissue flora. Skin and subcutaneous tissue flora of healthy individuals can be collected using swiping, scraping, swabbing, using tape strips or any other effective microbial collection method. The harvested sample can be profiled on a NGS, Sanger-sequencing, mass-spectrometry, quantitative PCR, immunofluorescence, in situ hybridization, or microbial staining based platform. For sequencing-based platforms, this can be done either using a whole-genome sequencing approach, or via targeted applications, a prominent example of which is 16S rDNA sequencing. All the above-mentioned identification methods can be implemented on samples directly collected from individuals without any proliferation step. This way, minimal bias is introduced toward identification of a mixture of culturable and unculturable microorganisms. A proprietary analysis algorithm can be used to identify species composition of each individual. A consensus healthy profile may be constructed from the healthy cohort. The healthy profile may be updated real time as more samples are collected over time. The healthy profile will serve as the reference for comparing all individual samples, i.e. profiles. Examples of identified bacteria belong to any phylum, including Actinobacteria, Firmicutes, Proteobacteria, Bacteroidetes. It will typically include common species such as *Propionibacteria, Staphylococci, Corynebacteria*, and *Acenitobacteria* species.

In an embodiment, the invention provides a platform or method for characterizing skin and subcutaneous tissue microbial flora of individuals with skin conditions Skin and subcutaneous tissue flora of individuals with skin conditions that are considered to be suboptimal can be collected using swiping, swabbing, tape strips or any other effective microbial collection method. Collected microbial sample can be profiled on a NGS, Sanger-sequencing, mass-spectrometry, quantitative PCR, immunofluorescence, in situ hybridization, or microbial staining based platform. For the sequencing based platforms, this can be done either using a whole-genome sequencing approach, or via targeted applications, a prominent example of which is 16S rDNA sequencing. All the identification methods can be implemented on samples directly collected from individuals without any proliferation step. This way, minimal bias is introduced toward identification of a mixture of culturable and unculturable microorganisms. A personal skin and subcutaneous tissue flora profile can be generated for each individual. Individuals, based on their phenotypic characteristics, can be placed under specific skin condition categories as well. Such clustering effort will help to identify biological significant patterns which are characteristic of each cohort. The microbial composition of the affected cohort is distinct from the healthy profile. Microbial species which are associated with any given skin condition can be used as early diagnostic markers for individuals who have not developed a visual skin condition but may be prone to that. Examples of identified bacteria belong to any phylum, including Actinobacteria, Firmicutes, Proteobacteria, Bacteroidetes. It will typically include common species, such as *Propionibacteria, Staphylococci, Corynebacteria*, and *Acenitobacteria* species. Damaged skin can impact the composition of bacterial flora or can cause nonpathogenic bacteria to become pathogenic.

In an embodiment, the invention provides a platform or method for characterizing a consensus healthy skin and subcutaneous tissue metabolite profile. The metabolome associated with skin and subcutaneous tissue flora can also be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance in a particular disease pathology. All the above-mentioned identification methods can be implemented on samples directly collected from individuals without any proliferation step. This way, minimal bias is introduced in the population composition. A proprietary analysis algorithm may be used to identify metabolite composition of each individual's skin flora. A consensus healthy profile may be constructed from the healthy cohort. The healthy profile may be updated real time as more samples are collected over time. The healthy profile will serve as the reference for comparing all individual samples, i.e. profiles.

In an embodiment, the invention provides a platform or method for characterizing skin and subcutaneous tissue microbial flora of individuals with skin conditions. Metabolite composition of skin and subcutaneous tissue flora of individuals with skin conditions that are considered to be suboptimal can be profiled either by a mass-spectrometry based system or using genomics-based metabolome modeling and flux-balance analysis. Extraction can be done on samples collected by using swiping, swabbing, tape strips or any other effective microbial collection method. Alternatively, those metabolites and biochemical, specifically the extracellular ones, can be directly isolated from any individual without going through any cell harvesting. Characterization can be done on the whole metabolome or only be focused on a subset of metabolites, which are known or may be shown to be of significance. All the above-mentioned identification methods can be implemented on samples directly collected from individuals without any proliferation step. This way, minimal bias is introduced in the population composition. A personal profile can be generated for each individual that reflects the metabolite composition of the skin and subcutaneous tissue flora. Individuals, based on their phenotypic characteristics, can be placed under specific skin condition categories as well. Such clustering effort will help to identify biological significant patterns that are characteristic of each cohort. The metabolite composition of the affected cohort is distinct from the healthy profile. Metabolites which are associated with any given skin condition can be used as early diagnostic markers for individuals who have not developed a visual skin condition but may be prone to that.

In an embodiment, the platform or method described herein may be provided as a test for profiling the skin flora of any individual, either healthy or with a skin condition and also their associated metabolome. Such test would be sensitive to characterize the dominant skin flora and metabolites of any individual. A customized or personalized evaluation of any individual's flora may be conducted and identified skin and subcutaneous tissue flora and metabolites may be compared to healthy and also affected skin profiles. A customized or personalized report may be generated which will specify species composition of the individual's skin and subcutaneous tissue flora and also its associated metabolites. Such report will enlist the beneficial and commensal species that are depleted or over-represented in each individual. It will also include the list of beneficial or undesired metabolites that are either depleted or over-represented in each individual. This may be used for formulation of the customized or personalized skin care or personal care product. Alternatively, the test can be administered to assess the performance of other skin care and personal care products, therapies, or evaluate any disruption of the normal skin flora or metabolites. The test can be performed before, during, and after any skin treatment in order to monitor the efficacy of that treatment regimen on skin flora or its associated metabolites. The test can also be used for early diagnostic of skin conditions that are associated with a signature microbial profile or their accompanying metabolites. The sensitivity of the test allows early diagnostic of such skin conditions before their phenotypic outbreak. In an aspect, the invention provides a method for generating, or a customized or personalized skin care or personal care product formulated for a particular individual. The customized or personalized product contains one or more beneficial or commensal microorganisms or a set of chemicals and metabolites which may be depleted in any given individual. Regular administration of such skin care products and personal care products should shift the suboptimal profile towards a healthy equilibrium. Skin care product may be applied after cleansing the existing flora with a proprietary lotion that will enhance the efficacy of colonization of skin care product microorganisms or its constituent metabolites. Any customized or personalized skin care or personal care product can contain one or more microorganisms, culturable or unculturable. The customized or personalized product can alternatively be a substrate and nutrients that favor the establishment or proliferation of mutualistic or commensal organisms and/or suppression of pathogenic organisms. Those chemicals and metabolites are either synthesized in vitro or purified from a microorganism.

Although the invention has been described with reference to the above examples, it will be understood that modifications and variations are encompassed within the spirit and scope of the invention. Accordingly, the invention is limited only by the following claims.

What is claimed is:

1. A method of characterizing and treating a skin disease, skin condition, or disorder of a subject, wherein said skin disease, said skin condition, or said skin disorder is acne, said method comprising:
    a) obtaining a sample comprising a plurality of microorganisms from a skin or subcutaneous tissue of said subject;
    b) performing sequencing on nucleic acid from said plurality of microorganisms thereby identifying a microbiome of said subject, and performing metabolome analysis on metabolites from said plurality of microorganisms thereby identifying a metabolome associated with said microbiome;
    c) characterizing said microbiome of said subject and said metabolome associated with said microbiome by comparing both said microbiome of said subject and said metabolome associated with said microbiome to a profile of a cohort of individuals, said profile comprising a representative microbiome and a representative metabolome, thereby generating a characterization of said subject comprising a determination of a similarity of said subject to said cohort of individuals; and
    d) administering a therapeutic formulation to said subject, said therapeutic formulation configured to modify both said microbiome of said subject and said metabolome associated with said microbiome to treat said acne, when said characterization indicates that said subject is in need of treatment for said acne.

2. The method of claim 1, further comprising comparing said microbiome of said subject to said representative microbiome.

3. The method of claim 1, further comprising generating a microbiome profile of said subject.

4. The method of claim 2, wherein said representative microbiome is classified as being indicative of said subject having a healthy profile, and wherein a similarity between said microbiome of said subject and said representative microbiome identifies said microbiome of said subject as being indicative of said subject having a healthy profile.

5. The method of claim 2, wherein said representative microbiome is classified as being indicative of said subject having, or being at risk of having, said acne, and wherein a similarity between said microbiome of said subject and said representative microbiome identifies said microbiome of said subject as being indicative of said subject having, or being at risk of having, said acne.

6. The method of claim 1, wherein said sample is obtained from said skin or said subcutaneous tissue via swipe, scrape, swab, biopsy, or tape.

7. The method of claim 6, wherein said tape is an adhesive tape.

8. The method of claim 1, wherein said plurality of microorganisms comprises bacteria, fungi, or a combination thereof.

9. The method of claim 8, wherein said plurality of microorganisms comprises a bacteria selected from the group consisting of Alphaproteobacteria, Betaproteobacteria, Gammaproteobacteria, Propionibacteria, Proteobacteria, Bacteroidetes, Corynebacteria, Actinobacteria, Clostridiales, Lactobacillales, *Staphylococcus, Bacillus, Micrococcus, Streptococcus*, Bacteroidales, Flavobacteriales, Firmicutes, *Enterococcus, Pseudomonas, Malassezia*, Maydida, Debaroyomyces, and *Cryptococcus*.

10. The method of claim 8, wherein said plurality of microorganisms comprises a bacteria of genus Propionibacteria, Staphylococci, Corynebacteria, or *Acinetobacter*.

11. The method of claim 1, wherein each individual of said cohort of individuals exhibits a particular phenotype or profile.

12. The method of claim 11, wherein each individual of said cohort of individuals has a microbiome that is similar to all other individuals of said cohort of individuals.

13. The method of claim 1, wherein said profile is based on samples from individuals having said acne.

14. The method of claim 1, wherein said therapeutic formulation is configured to promote growth and proliferation of one or more mutualistic or commensal microorganisms, or inhibit growth and proliferation of one or more pathogenic microorganisms.

15. The method of claim 1, wherein said subject has skin inflammation, and wherein said therapeutic formulation is configured to treat said skin inflammation.

16. The method of claim 15, wherein said skin inflammation is associated with sensitive skin.

17. The method of claim 1, wherein said subject does not have psoriasis.

18. The method of claim 1, wherein said therapeutic formulation comprises metabolites determined to be depleted in said subject based on said characterization.

19. The method of claim 1, wherein said therapeutic formulation is configured to shift said microbiome of said subject toward said representative microbiome and said metabolome associated with said microbiome toward said representative metabolome, wherein said cohort of individuals represents a healthy phenotype without said acne.

20. The method of claim 1, further comprising re-characterizing said microbiome of said subject and said metabolome associated with said microbiome subsequent to said administering of said therapeutic formulation to said subject.

21. The method of claim 1, wherein said therapeutic formulation comprises a substrate comprising nutrients that favor establishment or proliferation of one or more mutualistic or commensal microorganisms, or suppression of one or more pathogenic microorganisms.

22. The method of claim 1, wherein said characterization determines a subject cohort to which said subject belongs.

23. The method of claim 10, wherein said plurality of microorganisms comprises said bacteria of said genus Propionibacteria.

24. The method of claim 23, wherein said bacteria is *Propionibacterium acnes*.

25. The method of claim 24, wherein said therapeutic formulation is configured to inhibit growth and proliferation of said *Propionibacterium acnes*.

26. The method of claim 24, wherein said metabolites comprise short-chain fatty acids, propionic acid, or a combination thereof.

* * * * *